United States Patent
Kuo et al.

(10) Patent No.: US 9,636,513 B2
(45) Date of Patent: May 2, 2017

(54) DEFIBRILLATOR DEVICE

(71) Applicant: Winbond Electronics Corp., Taichung (TW)

(72) Inventors: Ming-Ying Kuo, Hsinchu (TW); Ming-Dou Ker, Hsinchu County (TW)

(73) Assignee: Winbond Electronics Corp., Taichung (TW)

( * ) Notice: Subject to any disclaimer, the term of this patent is extended or adjusted under 35 U.S.C. 154(b) by 0 days.

(21) Appl. No.: 14/601,830

(22) Filed: Jan. 21, 2015

(65) Prior Publication Data

US 2016/0206894 A1    Jul. 21, 2016

(51) Int. Cl.
*A61N 1/39* (2006.01)

(52) U.S. Cl.
CPC .............. *A61N 1/3981* (2013.01); *A61N 1/39* (2013.01); *A61N 1/3968* (2013.01); *A61N 1/3987* (2013.01)

(58) Field of Classification Search
CPC ....... A61N 1/39; A61N 1/3993; A61N 1/3968
See application file for complete search history.

(56) References Cited

U.S. PATENT DOCUMENTS

| 8,086,320 | B2 | 12/2011 | Saketkhou |
| 8,594,784 | B2 | 11/2013 | Schwibner et al. |
| 2003/0088275 | A1* | 5/2003 | Palmer ..................... A61B 5/04 607/5 |
| 2010/0318145 | A1 | 12/2010 | Chapman et al. |
| 2013/0304147 | A1 | 11/2013 | Aoyama et al. |
| 2014/0039594 | A1 | 2/2014 | Savage et al. |
| 2014/0222096 | A1 | 8/2014 | Hu et al. |

FOREIGN PATENT DOCUMENTS

| JP | 2002-360711 | 12/2002 |
| TW | M465735 U | 11/2013 |

OTHER PUBLICATIONS

JP Office Action dated Jan. 26, 2016 from corresponding JP Appl, 5 pp.

* cited by examiner

*Primary Examiner* — Joseph Dietrich
(74) *Attorney, Agent, or Firm* — Muncy, Geissler, Olds & Lowe, P.C.

(57) ABSTRACT

A defibrillator device is provided. The defibrillator device includes a first electrode, a second electrode, a readout module, a USB interface, a voltage converter and a stimulation module. When the first and second electrodes contact the chest of a patient, the readout module obtains a physiologic rhythm signal of the patient and provides a heart rhythm signal according to the first physiologic rhythm signal. According to a first voltage from a portable electronic device, the voltage converter generates a second voltage when the first USB interface is coupled to the portable electronic device, wherein the second voltage is larger than the first voltage. When the physiologic rhythm signal indicates that cardiac arrhythmia is present in the patient, the stimulation module provides an electric shock energy to the chest of the patient via the first and second electrodes according to the second voltage.

6 Claims, 4 Drawing Sheets

DEFIBRILLATOR DEVICE

BACKGROUND OF THE INVENTION

Field of the Invention

The invention relates to a defibrillator device, and more particularly to an Automated External Defibrillator (AED) system.

Description of the Related Art

In general, heart disease is a major cause of death. For example, arrhythmias caused by problems with the heart's electrical system result in an abnormal heart rhythm. The most serious arrhythmia is ventricular fibrillation (VF), which can cause the heart suddenly to stop pumping blood. Accordingly, the patient loses consciousness in a very short time. In addition, ventricular tachycardia (VT) and bradycardia can also lead to sudden cardiac arrest.

Usually, sudden cardiac arrest is unpredictable. When it strikes, the patient's heart will stop beating and he will stop breathing, and then lose consciousness. If the incident lasts more than 5 minutes, the survival rate of the patient drops to less than 50%. Therefore, what is needed is immediate Cardiopulmonary Resuscitation (CPR) and defibrillation, in order to avoid death and permanent damage.

Therefore, a defibrillator device that is easy to carry and use is desirable.

BRIEF SUMMARY OF THE INVENTION

An embodiment of a defibrillator device is provided. The defibrillator device comprises a first electrode; a second electrode; a readout module coupled to the first and second electrodes; a first USB interface; a voltage converter coupled to the first USB; and a stimulation module coupled to the first and second electrodes and the voltage converter. The readout module obtains a first physiologic rhythm signal of a patient when the first and second electrodes contact a chest of the patient, and provides a heart rhythm signal according to the first physiologic rhythm signal. According to a first voltage from a portable electronic device, the voltage converter generates a second voltage when the first USB interface is coupled to the portable electronic device, wherein the second voltage is higher than the first voltage. The stimulation module provides electric shock energy to the chest of the patient via the first and second electrodes according to the second voltage when the first physiologic rhythm signal indicates that cardiac arrhythmia is present in the patient.

Furthermore, an embodiment of a defibrillator system is provided. The defibrillator system comprises a portable electronic device and a defibrillator device. The defibrillator device comprises a first electrode, a second electrode, a readout module coupled to the first and second electrodes, a first USB interface, a voltage converter coupled to the first USB, and a stimulation module coupled to the first and second electrodes and the voltage converter. The readout module obtains a first physiologic rhythm signal of a patient when the first and second electrodes contact a chest of the patient, and provides a heart rhythm signal according to the first physiologic rhythm signal. According to a first voltage from the portable electronic device, the voltage converter generates a second voltage when the first USB interface is coupled to the portable electronic device, wherein the second voltage is higher than the first voltage. The stimulation module provides an electric shock energy to the chest of the patient via the first and the second electrodes according to the second voltage when the first physiologic rhythm signal indicates that cardiac arrhythmia is present in the patient.

A detailed description is given in the following embodiments with reference to the accompanying drawings.

BRIEF DESCRIPTION OF DRAWINGS

The invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
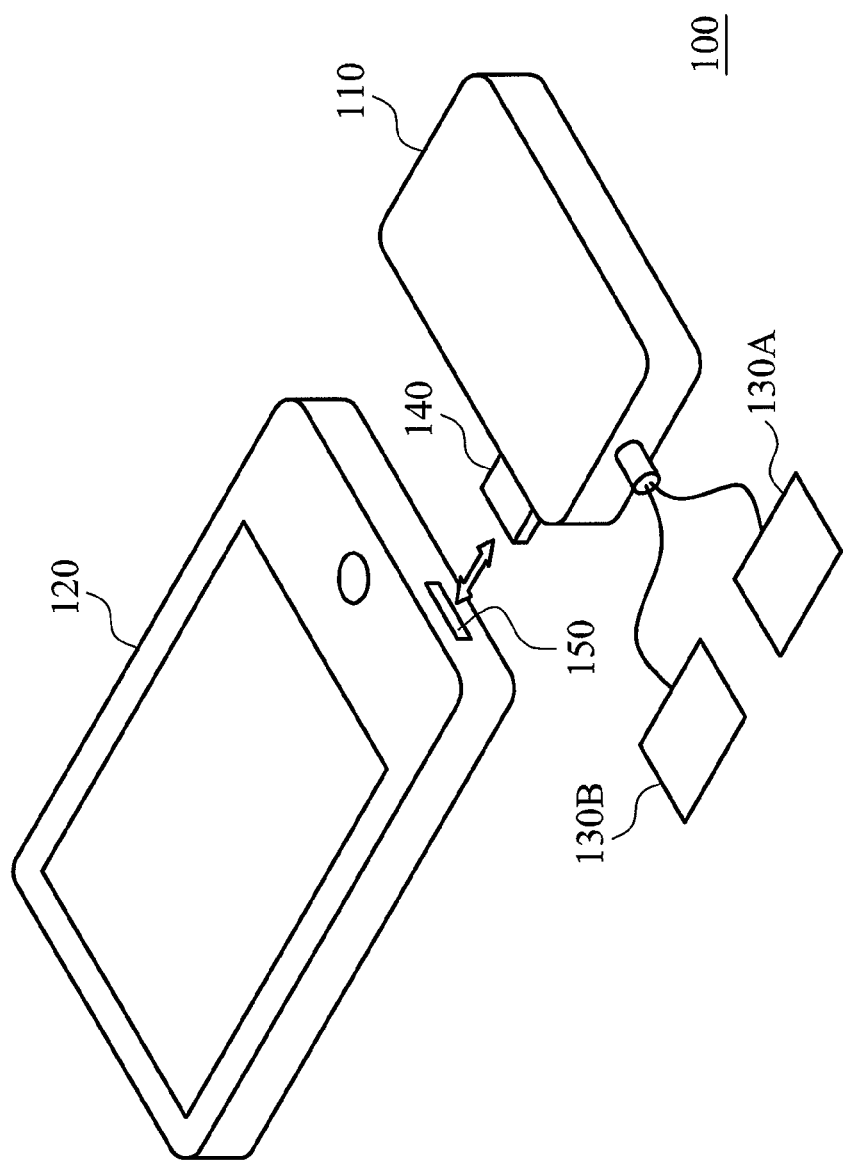
FIG. 1 shows an Automated External Defibrillator (AED) system according to an embodiment of the invention.

FIG. 1 shows an Automated External Defibrillator (AED) system 100 according to an embodiment of the invention. The AED system 100 comprises a defibrillator device 110 and a portable electronic device 120. In the embodiment, the portable electronic device 120 is a common universal mobile phone, which has a Universal Serial Bus (USB) interface 150, such as a receptacle that conforms to the Micro-USB standard. Furthermore, the defibrillator device 110 comprises an electrode 130A, an electrode 130B and a USB interface 140, e.g. a plug that conforms to the Micro-USB standard. Therefore, when the USB interface 140 of the defibrillator device 110 is coupled to the USB interface 150 of the portable electronic device 120, the defibrillator device 110 may function as an accessory to the portable electronic device 120 (i.e. a universal mobile phone). In other words, in the AED system 100, the portable electronic device 120 is a master device, and the defibrillator device 110 is a slave device. Therefore, when a patient feels chest pain, an operator can attach the electrodes 130A and 130B of the defibrillator device 110 to the skin on the chest of the patient near the heart, so that the defibrillator device 110 can measure a heart rhythm signal of the patient, and then the defibrillator device 110 transmits the heart rhythm signal to the portable electronic device 120 via USB transmission for analysis and judgment. Simultaneously, the portable electronic device 120 can fast-charge the defibrillator device 110 via the USB interfaces 140 and 150. If the portable electronic device 120 determines that the heart rhythm signal of the patient indicates a ventricular fibrillation of arrhythmia is present, the portable electronic device 120 controls the defibrillator device 110 to perform an electric shock procedure. During the electric shock procedure, the defibrillator device 110 provides electric shock energy to the chest of the patient via the electrodes 130A and 130B for defibrillation.

Figure 2:
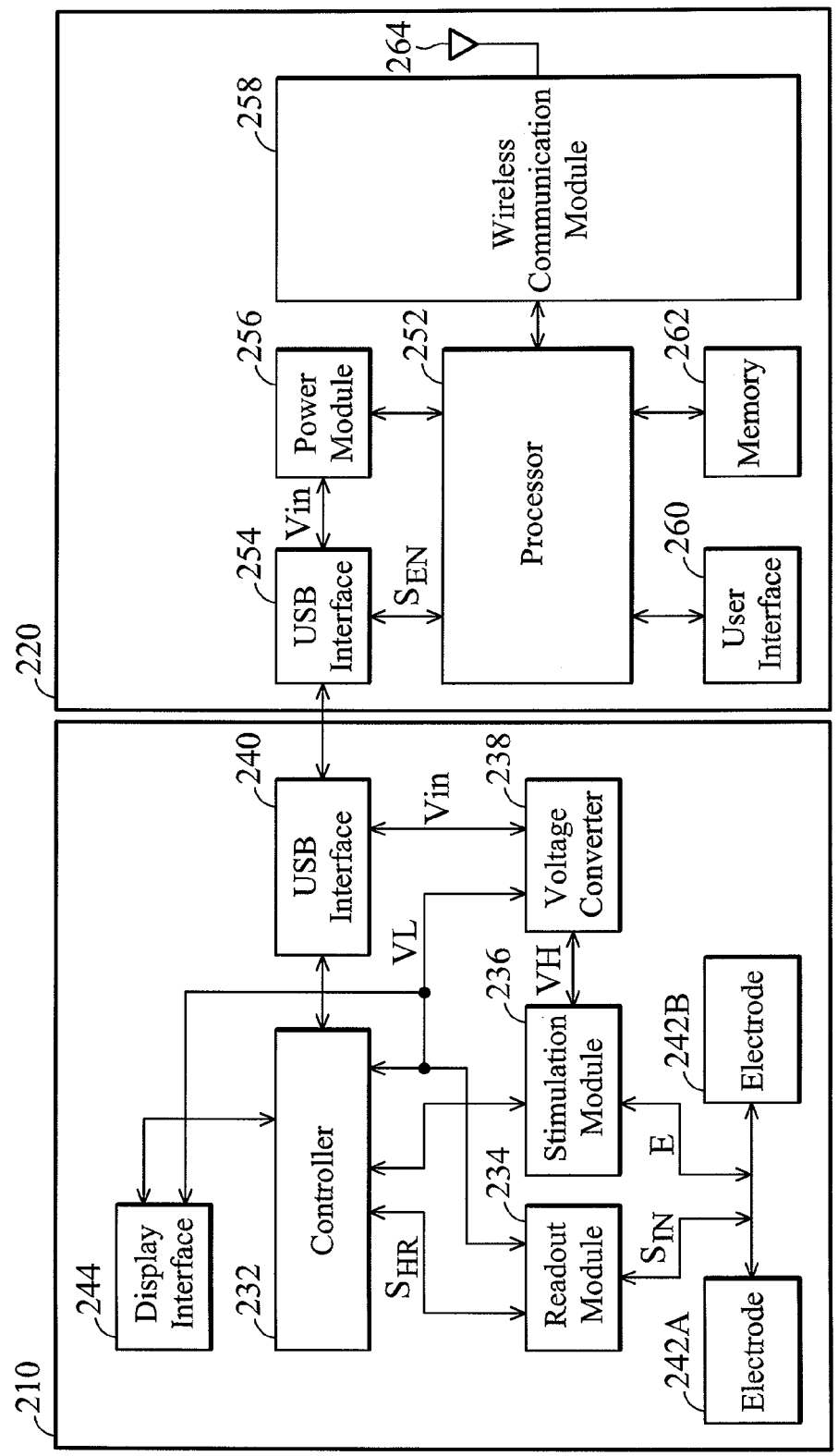
FIG. 2 shows an AED system according to another embodiment of the invention.

FIG. 2 shows an AED system 200 according to another embodiment of the invention. The AED system 200 comprises a defibrillator device 210 and a portable electronic device 220. As described above, the portable electronic device 220 may be a common universal mobile phone, and the defibrillator device 210 may be an accessory of a universal mobile phone. In the embodiment, the portable electronic device 220 comprises a processor 252, a USB interface 254, a power module 256, a wireless communication module 258, a user interface 260, a memory 262 and an antenna 264. The defibrillator device 210 comprises a controller 232, a readout module 234, a stimulation module 236, a voltage converter 238, a USB interface 240, the electrodes 242A and 242B, and a display interface 244. In FIG. 2, when the USB interface 240 of the defibrillator device 210 is coupled to the USB interface 254 of the portable electronic device 220, the portable electronic device 220 uses the power module 256 to provide a voltage signal Vin to the voltage converter 238 via the USB interfaces 254 and 240. Next, the voltage converter 238 generates a high voltage signal VH and a low voltage signal VL according to the voltage signal Vin. In FIG. 2, the voltage converter 238 provides the high voltage signal VH to the stimulation module 236, and the voltage converter 238 provides the low voltage signal VL to the controller 232, the readout module 234 and the display interface 244 as an operating voltage. In one embodiment, the high voltage signal VH is greater than the voltage signal Vin, and the voltage signal Vin is greater than the low voltage signal VL. Moreover, in one embodiment, the voltage converter 238 comprises a charge pump for generating the high voltage signal VH. The readout module 234 and the stimulation module 236 are both coupled to the electrode 242A and the electrode 242B. When the electrode 242A and the electrode 242B contact the chest of the patient, the readout module 234 obtains a physiologic rhythm signal $S_{IN}$ of the patient via the electrode 242A and the electrode 242B, and then provides a heart rhythm signal $S_{HR}$ to the controller 232 according to the physiologic rhythm signal $S_{IN}$. Next, the controller 232 transmits the heart rhythm signal $S_{HR}$ to the portable electronic device 220 via the USB interface 240.

In FIG. 2, when the USB interface 254 of the portable electronic device 220 is coupled to the USB interface 240 of the defibrillator device 210, in the portable electronic device 220, the processor 252 will control the power module 256 to provide the voltage signal Vin via the USB interface 254, so as to power the defibrillator device 210. Furthermore, in the portable electronic device 220, the processor 252 receives the heart rhythm signal $S_{HR}$ from the defibrillator device 210 via the USB interface 254, and stores the heart rhythm signal $S_{HR}$ into the memory 262. Next, the processor 252 analyzes and determines whether the heart rhythm signal $S_{HR}$ is normal, i.e. it is determined whether a ventricular fibrillation of arrhythmia is present in the patient according to the heart rhythm signal $S_{HR}$. If it is determined that the patient has arrhythmia, the processor 252 controls the defibrillator device 210 according to an AED application (AED APP) stored in the memory 262 to perform an electric shock procedure. When the electric shock procedure is performed, the processor 252 provides an enable signal $S_{EN}$ to the defibrillator device 210 via the USB interface 254. Next, in the defibrillator device 210, in response to the enable signal $S_{EN}$, the controller 232 controls the stimulation module 236 to generate electric shock energy E according to the high voltage signal VH, and provides the electric shock energy E to the patient via the electrodes 242A and 242B, so as to perform a defibrillation electric shock treatment for the patient. In one embodiment, the defibrillator device 210 may have a plurality of electrode pairs, wherein the defibrillator device 210 can use a first pair of electrodes (e.g. the electrodes 242A and 242B) to obtain the physiologic rhythm signal $S_{IN}$ of the patient, and use a second pair of electrodes (not shown) to provide the electric shock energy E to the patient. Next, the defibrillator device 210 will re-obtain the physiologic rhythm signal $S_{IN}$ of the patient via the electrodes 242A and 242B, and re-provide the heart rhythm signal $S_{HR}$ to the portable electronic device 22 according to the physiologic rhythm signal $S_{IN}$. Next, in the portable electronic device 220, the processor 252 determines whether the patient has recovered according to the re-obtained heart rhythm signal $S_{HR}$. If it is determined that the patient has a normal heart rhythm, the processor 252 stops the electric shock procedure. Conversely, if it is determined that the patient still has arrhythmia, the processor 252 continues controlling the defibrillator device 210 to perform the electric shock procedure until the patient has recovered. Furthermore, during the electric shock procedure, the processor 252 of the portable electronic device 220 may make an emergency call to an emergency rescue unit (e.g. a hospital or a fire station) via the wireless communication module 258 and the antenna 264, so as to communicate with first-aid personnel. Furthermore, the processor 252 may also provide the location of the patient to the emergency rescue unit via the wireless communication module 258 and the antenna 264. When the electric shock procedure is performed, the processor 252 may display an execution state of the electric shock procedure via the user interface 260. In one embodiment, the user interface 260 is a touch panel, which displays the execution state of the electric shock procedure and receives user instructions. For example, during the electric shock procedure, an operator can select a fully-automatic mode or a semi-automatic mode via the user interface 260. In the fully-automatic mode, the processor 252 automatically detects the physiologic rhythm signal $S_{IN}$ of the patient and provides an electric shock treatment on the patient until heart rhythm of the patient is normal. In the semi-automatic mode, the processor 252 provides the electric shock treatment to the patient after receiving instructions from the operator via the user interface 260. In the fully-automatic mode or the semi-automatic mode, the processor 252 displays a diagnosis of the heart rhythm signal $S_{HR}$ in the user interface 260. Thus, the operator can perform subsequent treatments (e.g. electric shock or hospitalization) according to the diagnosis.

Figure 3:
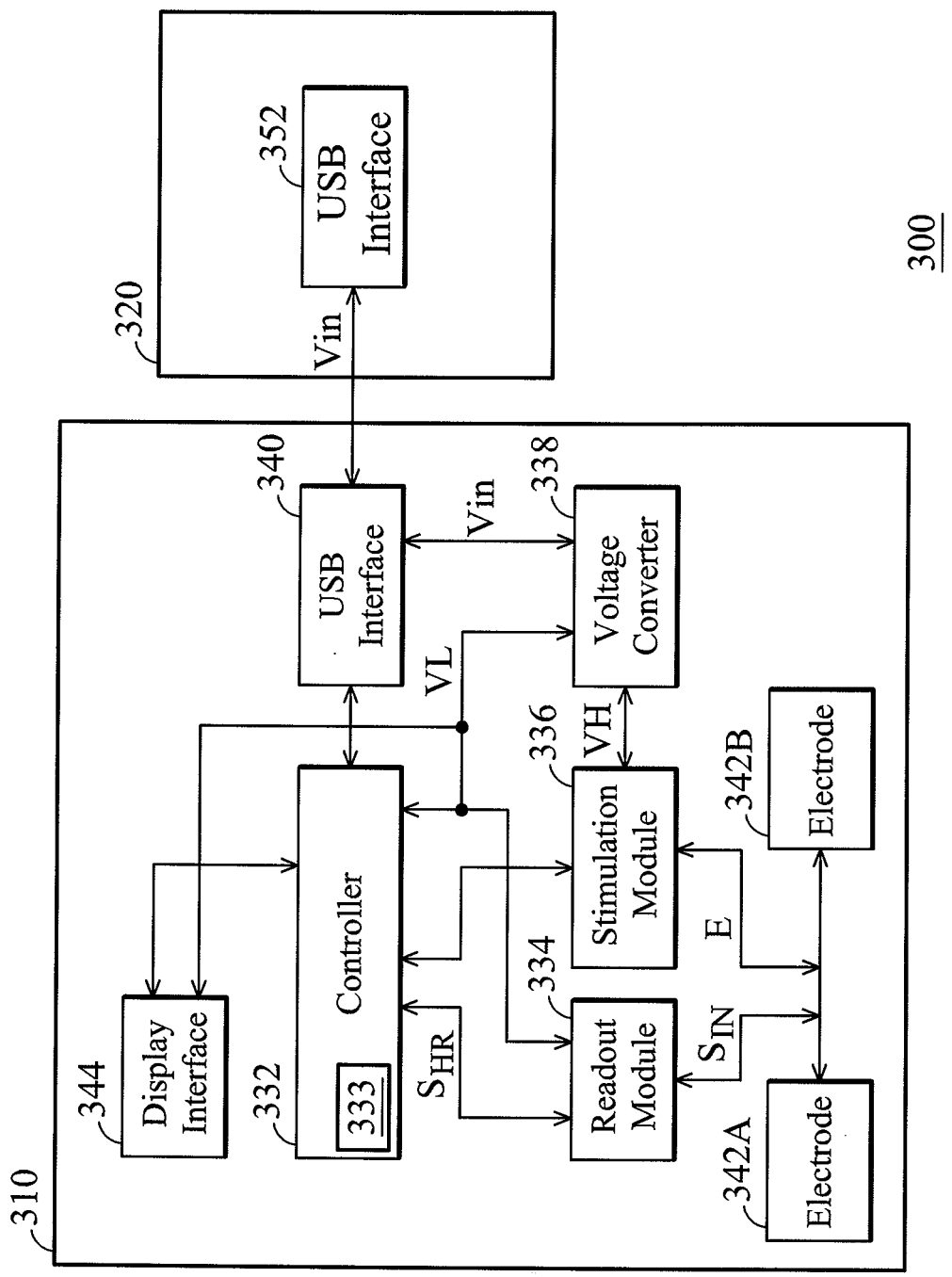
FIG. 3 shows an AED system according to another embodiment of the invention.

FIG. 3 shows an AED system 300 according to another embodiment of the invention. The AED system 300 comprises a defibrillator device 310 and a portable electronic device 320. In the embodiment, the portable electronic device 320 is a mobile power unit, which comprises a USB interface 352. The defibrillator device 310 comprises a controller 332, a readout module 334, a stimulation module 336, a voltage converter 338, a USB interface 340, the electrodes 342A and 342B and a display interface 344. When the USB interface 352 of the portable electronic device 320 is coupled to the USB interface 340 of the defibrillator device 310, the portable electronic device 320 provides the voltage signal Vin to the defibrillator device 310 via the USB interface 352, so as to power the defibrillator device 310. As described above, the voltage converter 338 provides a high voltage signal VH and a low voltage signal VL according to the voltage signal Vin from the USB interface 340. When the electrodes 342A and 342B contact the chest of the patient, the readout module 334 obtains the physiologic rhythm signal $S_{IN}$ of the patient via the electrodes 342A and 342B, and stores the heart rhythm signal $S_{HR}$ to a memory 333 of the controller 332 according to the physiologic rhythm signal $S_{IN}$. Next, the controller 332 analyzes and determines whether the heart rhythm signal $S_{HR}$ is normal, i.e. it is determined whether a ventricular fibrillation of arrhythmia is present in the patient according to the heart rhythm signal $S_{HR}$. If it is determined that the patient has arrhythmia, the controller 332 performs an electric shock procedure according to an AED application stored in the memory 333. Thus, the controller 332 controls the stimulation module 336 to generate an electric shock energy E according to the high voltage signal VH, and provides the electric shock energy E to the patient via the electrodes 342A and 342B, so as to perform a defibrillation electric shock treatment on the patient. Furthermore, when the electric shock procedure is performed, the controller 332 can display an execution state of the electric shock procedure in the display interface 344. In one embodiment, the controller 332 may continuously detect the physiologic rhythm signal of the patient, and provide the electric shock treatment on the patient until the heart rhythm of the patient is normal.

Figure 4:
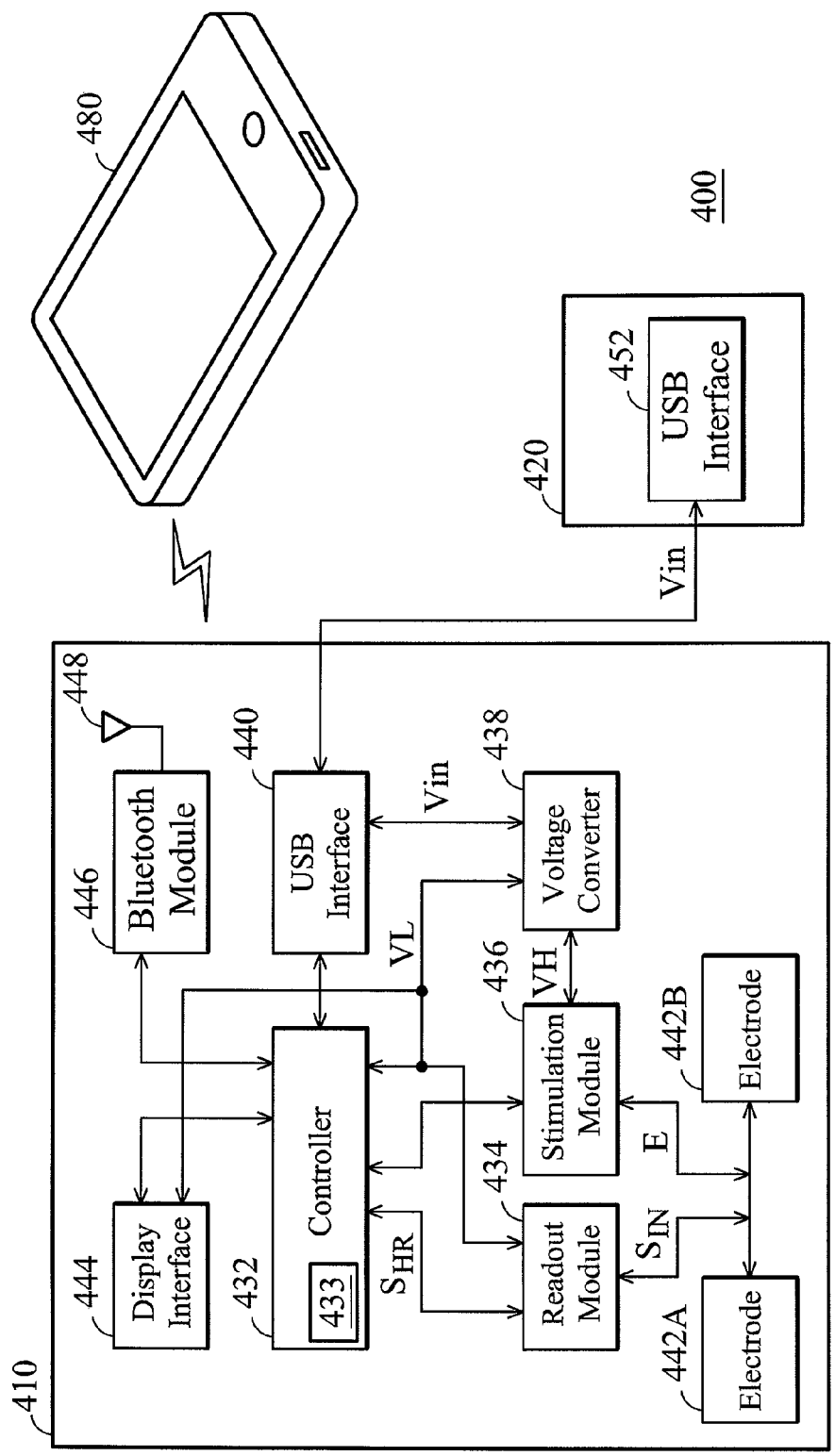
FIG. 4 shows an AED system according to another embodiment of the invention.

FIG. 4 shows an AED system 400 according to another embodiment of the invention. The AED system 400 comprises a defibrillator device 410, a portable electronic device 420 and a universal mobile phone 480 (e.g. the portable electronic device 120 of FIG. 1). In the embodiment, the portable electronic device 420 is a mobile power unit, which comprises a USB interface 452. Compared to the defibrillator device 310 of FIG. 3, the defibrillator device 410 further comprises a Bluetooth module 446 and an antenna 448, wherein the defibrillator device 410 communicates with a universal mobile phone 480 via the Bluetooth module 446 and the antenna 448. In the embodiment, the universal mobile phone 480 is a master device, and the defibrillator device 410 is a slave device. When the USB interface 452 of the portable electronic device 420 is coupled to the USB interface 440 of the defibrillator device 410, the portable electronic device 420 provides a voltage signal Vin to power the defibrillator device 410 via the USB interface 452. Next, the voltage converter 438 generates a high voltage signal VH and a low voltage signal VL according to the voltage signal Vin. As described above, when the electrodes 442A and 442B contact the chest of patient, the readout module 434 obtains a physiologic rhythm signal $S_{IN}$ of the patient via the electrodes 442A and 442B, and provides a heart rhythm signal $S_{HR}$ to the controller 432 according to the physiologic rhythm signal $S_{IN}$. Next, the controller 432 transmits the heart rhythm signal $S_{HR}$ to the universal mobile phone 480 via the Bluetooth module 446 and the antenna 448. Next, the universal mobile phone 480 receives the heart rhythm signal $S_{HR}$ from the defibrillator device 410 via the Bluetooth module and antenna thereof, and stores the heart rhythm signal $S_{HR}$ into the memory thereof. Next, the universal mobile phone 480 analyzes and determines whether the heart rhythm signal $S_{HR}$ is normal, i.e. it is determined whether a ventricular fibrillation of arrhythmia is present in the patient according to the heart rhythm signal $S_{HR}$. If it is determined that the patient has arrhythmia, the universal mobile phone 480 controls the defibrillator device 410 to perform an electric shock procedure according to an AED application stored in the memory thereof. When the electric shock procedure is performed, the universal mobile phone 480 provides an enable signal $S_{EN}$ to the defibrillator device 410 through a Bluetooth communication. Next, in the defibrillator device 410, in response to the enable signal $S_{EN}$, the controller 432 controls the stimulation module 436 to generates an electric shock energy E according to the high voltage signal VH, and provides the electric shock energy E to the patient via the electrodes 442A and 442B, so as to perform a defibrillation electric shock treatment on the patient. In one embodiment, the defibrillator device 410 may have a plurality of pair of electrodes, wherein the defibrillator device 410 can use a first pair of electrodes (e.g. the electrodes 442A and 442B) to obtain the physiologic rhythm signal $S_{IN}$ of the patient, and use a second pair of electrodes (not shown) to provide the electric shock energy E to the patient. Next, the defibrillator device 410 re-obtains the physiologic rhythm signal $S_{IN}$ of the patient via the electrodes 442A and 442B, and re-provides the heart rhythm signal $S_{HR}$ to the universal mobile phone 480 according to the physiologic rhythm signal $S_{IN}$. Next, the universal mobile phone 480 determines whether the patient has recovered according to the re-obtained heart rhythm signal $S_{HR}$. If it is determined that the patient has a normal heart rhythm, the electric shock procedure is stopped. On the contrary, if it is determined that the patient still has arrhythmia, the universal mobile phone 480 continues controlling the defibrillator device 410 to perform the electric shock procedure until the patient has recovered. Furthermore, during the electric shock procedure, the universal mobile phone 480 may call an emergency call to an emergency rescue unit, so as to communicate with first-aid personnel. Furthermore, the universal mobile phone 480 may also provide a location of the patient to the emergency rescue unit. When the electric shock procedure is performed, the universal mobile phone 480 may display an execution state of the electric shock procedure via the monitor thereof. Moreover, during the electric shock procedure, an operator can control the defibrillator device 410 to operate in a fully-automatic mode or a semi-automatic mode via the universal mobile phone 480.

According to the embodiments of the invention, a universal mobile phone and a defibrillator device capable of reading heart rhythm and outputting electric shock energy are used to form an AED system. In the embodiment, the defibrillator device (e.g. 110 of FIG. 1, 210 of FIG. 2, 310 of FIG. 3 and 410 of FIG. 4) may not need a built-in battery. A universal mobile phone or a mobile power unit can power the defibrillator device via the USB interface. In the embodiments of the invention, because the universal mobile phone, the mobile power unit and the defibrillator device are all slim and light, they are portable and able to promote security for lives of patients.

While the invention has been described by way of example and in terms of the preferred embodiments, it is to be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A defibrillator device, comprising:
   a first electrode;
   a second electrode;
   a readout module coupled to the first and second electrodes, obtaining a first physiologic rhythm signal of a patient when the first and second electrodes contact a chest of the patient, and providing a heart rhythm signal according to the first physiologic rhythm signal;
   a first USB interface;
   a voltage converter directly coupled to the first USB, wherein according to a first voltage from a portable electronic device via the first USB interface, the voltage converter generates a second voltage when the first USB interface is coupled to the portable electronic device, wherein the second voltage is higher than the first voltage;
   a stimulation module coupled to the first and second electrodes and the voltage converter, providing an electric shock energy to the chest of the patient via the first and the second electrodes according to the second voltage when the first physiologic rhythm signal indicates that cardiac arrhythmia is present in the patient;

a memory, storing an application; and a controller coupled to the first USB interface, the readout module and the stimulation module, receiving the heart rhythm signal from the readout module, and determining whether the cardiac arrhythmia is present in the patient according to the heart rhythm signal, wherein when the cardiac arrhythmia is present in the patient, the controller controls the stimulation module according to the application stored in the memory to provide the electric shock energy to the chest of the patient.

2. The defibrillator device as claimed in claim 1, wherein after the stimulation module provides the electric shock energy to the chest of the patient, the readout module re-obtains a second physiologic rhythm signal from the patient via the first and second electrodes, and the readout module provides a second heart rhythm signal according to the second physiologic rhythm signal, and the controller determines whether to continue performing the electric shock procedure according to the second heart rhythm signal, wherein when the second heart rhythm signal indicates that the heart rhythm of the patient is normal, the controller stops performing the electric shock procedure.

3. The defibrillator device as claimed in claim 1, further comprising:
   a display interface, displaying an execution state of the electric shock procedure.

4. The defibrillator device as claimed in claim 1, further comprising:
   a Bluetooth module, communicating with a mobile phone when the electric shock energy is provided to the chest of the patient, so as to provide the heart rhythm signal to the mobile phone, and to call an emergency call or provide a location of the patient to an emergency rescue unit.

5. The defibrillator device as claimed in claim 4, wherein the portable electronic device is a mobile power unit.

6. A defibrillator system, comprising:
   a portable electronic device; and
   a defibrillator device, comprising:
   a first electrode;
   a second electrode;
   a readout module coupled to the first and second electrodes, obtaining a first physiologic rhythm signal of a patient when the first and second electrodes contact a chest of the patient, and providing a heart rhythm signal according to the first physiologic rhythm signal;
   a first USB interface;
   a voltage converter directly coupled to the first USB, wherein according to a first voltage from the portable electronic device via the first USB interface, the voltage converter generates a second voltage when the first USB interface is coupled to the portable electronic device, wherein the second voltage is higher than the first voltage;
   a stimulation module coupled to the first and second electrodes and the voltage converter, providing an electric shock energy to the chest of the patient via the first and the second electrodes according to the second voltage when the first physiologic rhythm signal indicates that cardiac arrhythmia is present in the patient;
   a memory, storing an application; and
   a controller coupled to the first USB interface, the readout module and the stimulation module, receiving the heart rhythm signal from the readout module, and determining whether the cardiac arrhythmia is present in the patient according to the heart rhythm signal,
   wherein when the cardiac arrhythmia is present in the patient, the controller controls the stimulation module according to the application stored in the memory to provide the electric shock energy to the chest of the patient,
   wherein the portable electronic device is a mobile power unit.

* * * * *